(12) United States Patent
Berneking et al.

(10) Patent No.: US 10,901,056 B2
(45) Date of Patent: Jan. 26, 2021

(54) HYBRID IMAGING APPARATUS

(71) Applicant: Bruker BioSpin MRI GmbH, Ettlingen (DE)

(72) Inventors: Arne Berneking, Karlsruhe (DE); Sven Junge, Ettlingen (DE)

(73) Assignee: BRUKER BIOSPIN MRI GMBH, Ettlingen (DE)

( * ) Notice: Subject to any disclaimer, the term of this patent is extended or adjusted under 35 U.S.C. 154(b) by 0 days.

(21) Appl. No.: 16/505,980

(22) Filed: Jul. 9, 2019

(65) Prior Publication Data
US 2020/0011948 A1    Jan. 9, 2020

(30) Foreign Application Priority Data

Jul. 9, 2018   (DE) .......................... 10 2018 211 279

(51) Int. Cl.
| G01R 33/422 | (2006.01) |
| G01R 33/48 | (2006.01) |
| G01T 1/29 | (2006.01) |

(52) U.S. Cl.
CPC ......... *G01R 33/422* (2013.01); *G01R 33/481* (2013.01); *G01T 1/2985* (2013.01)

(58) Field of Classification Search
CPC .. G01R 33/422; G01R 33/481; G01T 1/2985; G01T 1/1603; A61B 6/037; A61B 6/4258; A61B 6/4417; A61B 5/055
See application file for complete search history.

(56) References Cited

U.S. PATENT DOCUMENTS

| 7,667,457 B2 | 2/2010 | Linz et al. |
| 7,728,590 B2 * | 6/2010 | Eberler ................. A61B 5/055 324/318 |

(Continued)

FOREIGN PATENT DOCUMENTS

| DE | 102005015070 A1 | 10/2006 |
| DE | 102013108497 A1 | 2/2015 |
| WO | 2015018894 A1 | 2/2015 |

OTHER PUBLICATIONS

Berneking et al., "Design and Characterization of a Gradient-Transparent RF Copper Shield for PET Detector Modules in Hybrid MR-PET Imaging",(2017), pp. 1-11.

(Continued)

*Primary Examiner* — Susan S Lee
(74) *Attorney, Agent, or Firm* — Edell, Shapiro & Finnan, LLC

(57) ABSTRACT

A hybrid imaging apparatus includes a magnetic resonance imaging (MM) arrangement having an RF resonator structure (1) and a gradient coil system (8) having a longitudinal axis, an emission tomography (ET) arrangement with a detector device having at least one photosensor (3) and one circuit board arrangement with at least one readout circuit board (11) on which an ET electronics is arranged, and an internal shielding device (7) shielding the readout electronics (4) of the ET arrangement and shielding the RF resonator structure of the MRI arrangement. The photosensor is arranged, in relation to the longitudinal axis, radially inside the sensor circuit boards and radially outside the RF resonator structure. The internal shielding device is arranged radially outside the photosensor and/or integrated into the photosensor. This achieves both a compact design and optimized performance of the detection of the MR and ET imaging.

15 Claims, 9 Drawing Sheets

(56) References Cited

U.S. PATENT DOCUMENTS

| | | | |
|---|---|---|---|
| 9,072,451 | B2 | 7/2015 | Benlloch Baviera et al. |
| 9,817,095 | B2* | 11/2017 | Corbeil ................. G01R 33/42 |
| 2006/0251312 | A1 | 11/2006 | Krieg et al. |
| 2006/0293580 | A1 | 12/2006 | Ladebeck et al. |
| 2010/0033186 | A1 | 2/2010 | Overweg |
| 2013/0211233 | A1 | 8/2013 | Yamaya et al. |
| 2013/0296689 | A1* | 11/2013 | Okamoto ............. A61B 6/4417 |
| | | | 600/411 |
| 2014/0264041 | A1 | 9/2014 | Schulz et al. |

OTHER PUBLICATIONS

Berneking et al., "RF Coil Performances in Compact Hybrid MR/PET Scanner Design Using an Integrated Shielding", (2017), 15 pages.

Parl et al., "A novel optically transparent RF shielding for fully integrated PET/MRI systems", iopscience.iop.org, (2017), 23 pages.

Truhn et al., "Optimized RF shielding techniques for simultaneous PET/MR", (2011), 7 pages.

Salomon et al., "Sparse crystal setting and large axial FOV for integrated whole-body PET/MR", 2011 IEEE Nuclear Science Symposium Conference Record, 3 pages.

Berneking et al., "A new PET detector concept for compact preclinical high-resolution hybrid MR-PET" Nuclear Inst. and Methods in Physics Research, A 888 (2018), pp. 44-52.

* cited by examiner

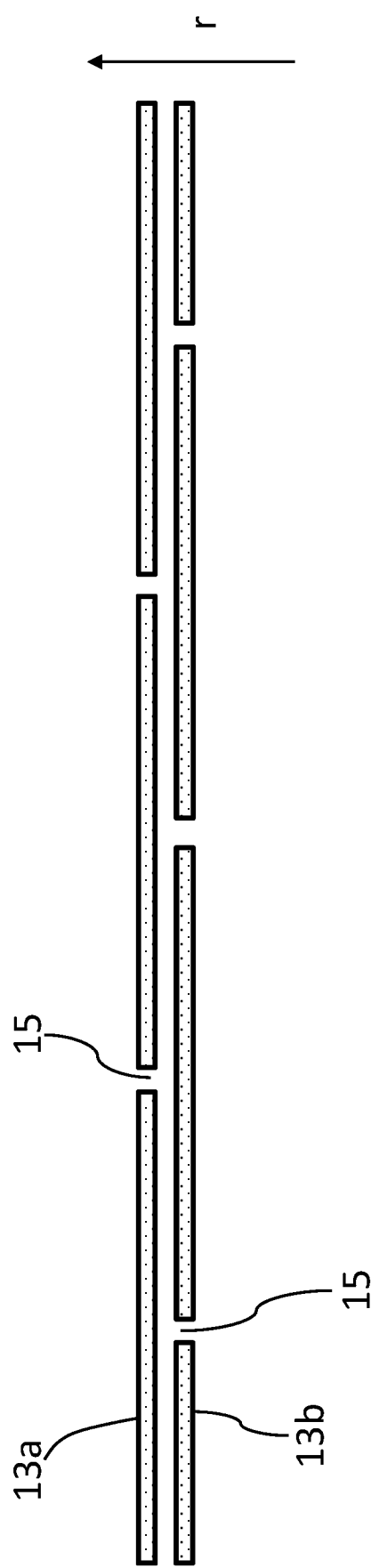

HYBRID IMAGING APPARATUS

This application claims foreign priority under 35 U.S.C. § 119(a)-(d) to German Application No. 10 2018 211 279.7 filed on Jul. 9, 2018, the entire contents of which are hereby incorporated into the present application by reference.

FIELD OF THE INVENTION

The invention relates to a hybrid imaging apparatus comprising a magnetic resonance imaging (MM) arrangement having an RF resonator structure and a gradient coil system having a longitudinal axis, an emission tomography (ET) arrangement with a detector device comprising at least one photosensor and one circuit board arrangement, wherein the circuit board arrangement comprises at least one readout circuit board on which an ET electronics is arranged, an internal shielding device for mutually shielding the ET electronics of the ET arrangement and the RF resonator structure of the MM arrangement, wherein the photosensor is arranged, in relation to the longitudinal axis, radially inside the circuit board arrangement and radially outside the RF resonator structure.

BACKGROUND

Such a hybrid imaging apparatus is known, for example, from [3].

One of the greatest challenges when designing MR/ET hybrid scanners is the suppression of interference and mutual influences of components of both imaging modalities. In MR/PET hybrid scanners, for example, PET components interact with the sensitive magnetic fields of the MM, and additionally, the strong magnetic fields of the MRI arrangement, the static $B_0$ field and the gradient fields, influence PET electronics and thus PET data acquisition.

In addition, electromagnetic interference occurs. RF coils are matched to the Larmor frequency and generate a magnetic field $B_1$ in the megahertz range with an amplitude in the µT range perpendicular to the $B_0$ orientation to excite spins. Due to the high frequency, the generation of an electrical field component cannot be prevented. The power here reaches the kW range and disturbs the PET electronics. Moreover, RF coils are capable of detecting very small signals of excited spins, wherein a receive signal can lie in the µV range. For this reason, MRI coils are very susceptible to noise and can detect even the smallest (disturbing) signals if these are in the region of the Larmor frequency of the MRI scanner. Since modern MR/PET scanners contain a multiplicity of electronic elements, inter alia FPGA, ASIC and various signal lines in the MHz range, and even digitization of the PET data in the MRI scanner can occur with broadband noise, transmitted signals of the PET electronics can disturb the reception signal of the RF coil or completely superpose it such that detection of the MR signals is impossible. An MRI arrangement is always shielded by way of suitable measures, for example with a Faraday cage, for the same reason.

As a consequence, shielding systems of the PET electronics having a high shielding factor are required for combined MR and PET systems. The same is true if electronics other than PET electronics, such as SPECT (single photon emission computed tomography) electronics, are installed in the shielded examination space. For this reason, an additional shielding system of the electronics of these combined systems is always required in the examination space within the Faraday cage.

For this reason, there is typically a shielding system against the electromagnetic fields around the PET electronics. The shielding strength is here dependent on the electrical conductivity. The greater the conductivity, the greater the shielding factor. For this reason, metals or carbon are typically used as the shielding material. It should be noted here that the shielding system should not interact with the gradient fields. If the gradient coils are switched on and off, which happens during every MRI examination, eddy currents are induced on the surfaces of the shielding system. The eddy currents that are induced themselves generate a magnetic field that superposes the gradient fields and thus disturbs the phase and frequency coding and consequently ultimately the spatial resolution of the MM images. This can likewise result in undesirable heat generation due to said eddy currents. This is particularly critical for MM sequences with a high duty cycle such as EPI, EPIK or diffusion imaging, in which gradient coils are switched as quickly as possible and frequently successively with a high gradient amplitude.

In addition to the shielding system of the PET electronics, a shielding system of the RF transmission and receive coil is also provided in known MR/PET hybrid scanners to suppress any influence of the environment on the resonance circuits of the RF coil. A suitable, slotted copper shield that is transparent for the gradient fields and at the same time functions in a manner of a closed conductor in the radio-frequency range is typically used here.

A PET arrangement is typically present in the form of a PET ring, but other geometries are also possible. Frequently, PET rings are constructed in the form of cassettes. In this case, the PET detectors (generally with scintillation crystals), the PET readout electronics and PET preprocessing are located inside a cassette. A ring is then composed of a multiplicity of cassettes. It is typical here to place a copper shield onto the cassette housing or to produce the cassette housing from carbon. Alternatively, completely electrically closed PET rings are used. In conventional systems, a shield that suppresses mutual influences of PET electronics and MR-RF coils is installed as the shielding system around the PET ring. Moreover, it is known to optimize the shielding system by structuring and constructing a frequency-selective shielding system such that it has maximum attenuation at the Larmor frequency and at the same time minimally influences gradient fields [12]. A concept for such PET cassettes is described in [1].

The conventional construction methods require an RF coil shield for the RF coil and an additional shielding system of the PET electronics. A corresponding amount of space is required herefor in the magnet bore, but this is limited and expensive. In addition, the RF coil shield requires a specific distance from the RF coil because it has a substantial influence on the performance of the coil [2].

In MRI and in particular MR/PET system development, the goal for cost reasons is to attain a design that is as compact as possible. The smaller the diameter of the MR magnet, the lower the price for said MR system. It is additionally advantageous to bring both the MRI receive coil and the PET detectors as closely as possible to the examination object to obtain an optimum signal-to-noise ratio of the detectors of the MR and PET imaging and at the same time save on PET detectors. There is therefore interest with advancing integration that PET detectors with electronics and shielding are located increasingly more closely to the examination object. In order to prevent disturbing changes in the gradient fields in the examination object with image disturbances and image artefacts, the shielding measures must be suitable for substantially suppressing eddy currents.

In order to realize such a compact design, it has been proposed to integrate the RF coil shield in the inner PET shielding system (integrated shielding system), cf. [2]. The additional small space saving can here be used to optimize the distance between the integrated shielding system and RF coil, such that the RF coil exhibits better performance. Gradient-influence-reducing methods as described under [1] or other known methods can likewise be employed for these integrated shielding systems.

A further and significantly greater space-saving is obtained if the integrated shielding system is arranged behind the scintillator crystals of the PET detectors, because the distance of the RF coil from the integrated shielding system can thus be occupied by the scintillator crystals. [3], [4], [9] and [11] therefore propose to arrange the integrated shielding system between scintillator crystals and photosensors.

However, these arrangements have the disadvantage that the layer for the integrated shielding system is positioned between the scintillation crystal and photosensor. This results in optical attenuation and reduced input coupling of photons between the scintillation crystal and photosensor. The layer must therefore additionally be very thin, because otherwise even more photons are absorbed. As a consequence, the shielding strength is significantly reduced as compared to a conventional shield. [9] additionally proposes to place a metal grid between SiPM sensors. This in turn is merely a shielding grid with low shielding strength or a shield grid with suitable electrical shield effect and suboptimum optical properties. In addition, the photosensors cannot be arranged in series with arbitrary density, which necessarily results in sensitivity losses due to the optical attenuation of the PET ring.

One concept for dividing the scintillator crystals and applying copper faces in the intermediate faces and connecting them is known from [6] and [10]. However, the disadvantage here is that the shielding system is arranged between the crystals and the latter must be divided.

A further concept is known from [7] and [8]. Here, different shielding materials are inserted between the scintillation crystals. This concept is suitable only when a pixelated scintillator array is used and the grid of the shield is present at the size of the pixelated crystals. It is not suitable for monolithic crystals. Moreover, the shielding strength is typically significantly lower than that of a closed shield. Furthermore, the PET detector geometry must here be adapted to the shielding concept such that for example free selection of the pitch spacing of the scintillator array and the length of the scintillation crystals is no longer possible.

SUMMARY

It is therefore an object of the invention to propose a hybrid imaging apparatus which has a compact design and with which an optimized signal-to-noise ratio of the detection of the MR and ET imaging can additionally be achieved.

This object is achieved according to one aspect of the invention by virtue of the internal shielding device being arranged, in relation to the longitudinal axis, radially outside the photosensor and/or being integrated into the photosensor.

In the case of the hybrid imaging apparatus according to the invention, a common integrated internal shielding device is used for shielding the ET electronics against the RF coil and for shielding the RF coil against the ET electronics. Said integrated internal shielding device is arranged between the RF resonator arrangement and ET electronics, but, in contrast to the shielding devices known from the prior art, not between the photosensor and RF resonator structure but according to the invention radially outside the photosensor or in the photosensor. "Radial" is always in relation to directions perpendicular to the longitudinal axis of the MRI arrangement, with "radially outside" meaning: with a greater distance from the z-axis. In this way, a compact design can be realized because, in the case of a detector device containing scintillation crystals, the scintillation crystals can be positioned closely to the examination object. Due to the positioning of the internal shielding device radially outside of the photosensor or in the photosensor, as per the invention, photons that are to be detected are prevented from being blocked by the shielding system and from reaching the photosensor. As a result, the optical properties of the detector device can be prevented from being influenced. The result is thus improved performance of the hybrid imaging apparatus because the optical properties of the detector device do not need to be changed. An arrangement with scintillation crystals in which, due to scintillation, low-energy photons (that is to say photons in the UV, near infrared or visible wavelength range) are produced that are then detected in the photosensor can be used as the detector device. Alternatively, a sensor for detecting high-energy photons (gamma radiation) can be used as the photosensor, for example gas detectors or semiconductor detector. In this case, the high-energy photons produced in the emission tomography can be detected. In the latter case, no scintillation crystals are required in the apparatus according to the invention.

The internal shielding device preferably has the same cross-sectional shape as the ET arrangement, in particular an annular or square cross section.

The material of the internal shielding device is not ferromagnetic and preferably comprises copper, silver-clad copper, or silver.

In a preferred embodiment of the hybrid imaging apparatus according to the invention, the emission tomography arrangement is a positron emission tomography (PET) arrangement, wherein the detector device comprises a plurality of photosensors (preferably arranged in the shape of a circle). Alternatively, a SPECT arrangement can be used as the emission tomography arrangement.

The internal shielding device should have a sufficiently high capacitance such that for the internal shielding device a resistance of less than 1Ω in the MHz range is reached and at the same time a resistance of >1 kΩ in the kHz range. The setting of the capacitance is preferably realized using overlapping surfaces made of electrically conductive material. In a particularly preferred embodiment, the internal shielding device therefore comprises a plurality of, preferably overlapping, shielding faces made of electrically conductive material. In the overlap region it is necessary for an insulator, preferably a dielectric, to be located between the shielding faces.

A particularly simple implementation and realization of a frequency-selective shielding system can be realized by virtue of the shielding faces being integrated in at least one circuit board of the circuit board arrangement or being placed on at least one circuit board of the circuit board arrangement, wherein the at least one circuit board is/are a readout circuit board(s) and/or sensor circuit board(s) of the ET arrangement. The readout circuit board comprises the ET electronics and possibly the photosensor. The photosensor, however, can also be placed on a dedicated sensor circuit board. The shielding faces that form the internal shielding device are preferably arranged in and/or on the same circuit board of the circuit board arrangement (that is to say in/on the sensor circuit board or in/on the readout circuit board).

The readout circuit boards and possibly the optional sensor circuit boards are arranged radially outside or at the same radial position as the internal shielding device.

The internal shielding device preferably comprises at least one electrically conductive circuit board layer (layer of the sensor circuit boards and/or readout circuit boards). Alternatively or additionally, at least one additional electrically conductive layer can be placed as the shielding face on the circuit boards. Due to the integration according to the invention of the internal shielding device in the circuit board arrangement or the sensor element, it is possible to dispense with an additional housing for the ET arrangement on which for example a copper layer for shielding purposes must be applied.

The circuit board arrangement preferably includes multiple layers and comprises at least partially a plurality of shielding faces, wherein the different shielding faces are distributed within the circuit board arrangement over a plurality of layers of the circuit board arrangement. A shielding system over a plurality of circuit board layers is therefore designed. By using a plurality of layers for the internal shielding device, the shielding strength can be considerably increased. As an alternative, the shielding layers that should typically have a thickness of 10 times the skin depth of the corresponding Larmor frequency can be embodied to be thinner. It has been shown in [5] that dividing the layer thickness into a plurality of layers does not significantly reduce the shielding strength. When using a plurality of thin layers, however, the gradient eddy currents decrease as compared to a thicker layer.

In a preferred embodiment, the shielding faces within a circuit board of the circuit board arrangement are capacitively interconnected. The capacitances are here preferably selected such that the lowest possible resistance is obtained in the radio frequency range in the range of the Larmor frequency (1 MHz to 10 GHz depending on the field strength $B_0$) and the highest possible resistance in the low-frequency range (kHz). The capacitive connection of the shielding faces within a circuit board can also be realized by way of capacitors soldered onto the corresponding circuit board. The capacitors can be soldered for example onto the rear side of the sensor circuit boards or onto the front side or rear side of the readout circuit board. If the shielding layers are not situated on the same side of the circuit board on which the capacitors are located, contact can be established by way of vias.

Instead of soldered-in capacitors, the capacitances can also be realized with the aid of two or more shielding layers within the circuit board arrangement. In a particularly preferred embodiment, the capacitive connection of the shielding faces within the circuit board arrangement is therefore realized by way of overlaying the shielding faces within the circuit board arrangement, in particular within a circuit board of the circuit board arrangement. Depending on the capacitance that is desired, the degree of overlap of the shielding faces can be determined in accordance with the formula $C=\varepsilon_0\varepsilon_r A/d$. It is thus possible by way of the selection of the dielectric and consequently of the relative permittivity $\varepsilon_r$, the size of the overlap areas and of the distance of the overlap areas to set a capacitance that represents impedances of different magnitude in dependence on frequency and frequency-dependent attenuations.

The internal shielding device preferably forms a closed RF shield face. A "closed RF shield face" is understood to mean a shielding that produces shielding that is closed in itself for electromagnetic waves and is impenetrable at all locations of the shielding device in the high-frequency range (1 MHz to 10 GHz). The circuit boards can to this end be soldered to one another with a conductive material or be brought into electrical contact using compression connection or plug connection, whereby, however, eddy currents can be induced for example by switching the gradient coils.

The closed RF shield face can furthermore be realized by virtue of the internal shielding device having integrated capacitances between the individual shielding faces. In this way, capacitive coupling of the shielding faces is achieved, and the RF shield face can be expanded to a plurality of circuit boards of the circuit board arrangement and thus forms a closed RF shield face. One option for realizing this is to connect the shield faces of different circuit boards by way of capacitors that have been soldered in or by an overlap of the shield faces similarly to a plate capacitor. The capacitances of the capacitors or of the capacitive coupling are selected such that a low impedance is given in the RF range, that is to say the internal shielding device in the range of the Larmor frequency is suitably conductive, and a high impedance is present in the kHz range of the gradients. This ensures high shielding of the RF signal in the range of the Larmor frequency of the MM arrangement. In addition, the faces for induced gradient currents (eddy currents) are made smaller, reducing eddy current strengths.

In addition, an external shielding device arranged radially outside of the detector device and the circuit board arrangement is preferably present. The external shielding device shields the ET electronics in the radially inner direction. In order to form a completely closed shield (that is to say a shield that completely surrounds the ET electronics on all sides), the internal shielding device and the external shielding device are electrically connected or electromagnetically, in particular capacitively or inductively, coupled preferably at the peripheries (axial ends).

In a preferred embodiment, components of the ET electronics are arranged radially between the internal shielding device and external shielding device. If the internal shielding device is integrated in the readout circuit boards containing the ET electronics, the components of the ET electronics are consequently arranged on the side of the readout circuit boards that face the external shielding device. Signal and supply lines of the ET electronics are preferably arranged between the internal shielding device and external shielding device. Consequently, the ET electronics can be shielded optimally.

According to a specific embodiment, the internal shielding device is integrated in at least one sensor circuit board of the circuit board arrangement and the at least one sensor circuit board is provided with vias for signal and supply lines, or the internal shielding device is integrated in the photosensor and the photosensor is provided with vias through the internal shielding device that is integrated in the photosensor to guide through the output signals and supply voltages. The vias are used to connect the photosensor or the sensitive part of the photosensor that is always located radially inside the internal shielding device (that is to say outside the shielded region) to the ET electronics and to read it. In particular, through-silicon vias (TSV) or through-glass vias (TGV) are suitable herefor. The most direct connection (that is to say along the shortest path) can be realized with TSV and TGV. In this way, the signal line lengths and again the regions in which disturbing signals can be input coupled can be reduced. Moreover, it is possible in this embodiment for the signal lines of the photosensors to be guided directly under the photosensors through the sensor circuit board and the internal shielding device, with the result that the signal line presence above the internal shielding device is minimized.

In order to suppress input coupling of disturbing signals into and through the closed RF shield face, it is advantageous if the hybrid imaging apparatus comprises RF filters that are arranged (in the radial direction) directly in front of or behind the internal shielding device.

Alternatively and with preference, said RF filters can also be integrated directly in the internal shielding device or in the circuit board arrangement, in particular within a circuit board.

If the internal shielding device is integrated directly in the detector device, the RF filters are preferably integrated in the photosensors per se or in the signal output of the photosensors. As a result, the efficiency of the shielding can be increased further.

The filters that can be selected can be the filter types known to a person skilled in the art such that signals in the MHz to GHz range (corresponding to the Larmor frequency) are blocked. These filters can be, for example (although not exclusively), low-pass, bandpass and high-pass filters, in particular third order low-pass filters and notch filters.

The detector device is preferably a silicon photomultiplier (SiPM). In principle, the shielding principle according to the invention can be employed in different detector devices, but the use of SiPM is preferred because the latter are less sensitive towards RF radiation on account of their high intrinsic gain. The output signal is then less susceptible to disturbances.

Circuit board materials that are known to the person skilled in the art or for example glass circuit boards can be used as the circuit boards in which the internal shielding device is integrated. The shielding layers can be integrated in the glass circuit boards in the form of copper layers. This achieves additional space saving because the RF filters are miniaturized and can be integrated at a smaller size than in conventional circuit boards directly as a copper structure in the glass circuit board.

Further advantages of the invention are apparent from the description and the drawing. The aforementioned features and the features mentioned below can likewise be employed according to the invention in each case individually by themselves or in any desired combination. The embodiments shown and described should not be understood to be an exhaustive list, but rather have an exemplary character for the purpose of illustrating the invention.

BRIEF DESCRIPTION OF THE DRAWINGS

FIG. 9 shows a sectional view of a detail of an internal shielding device having overlapping shielding faces (longitudinal section).

DETAILED DESCRIPTION

Figure 1:
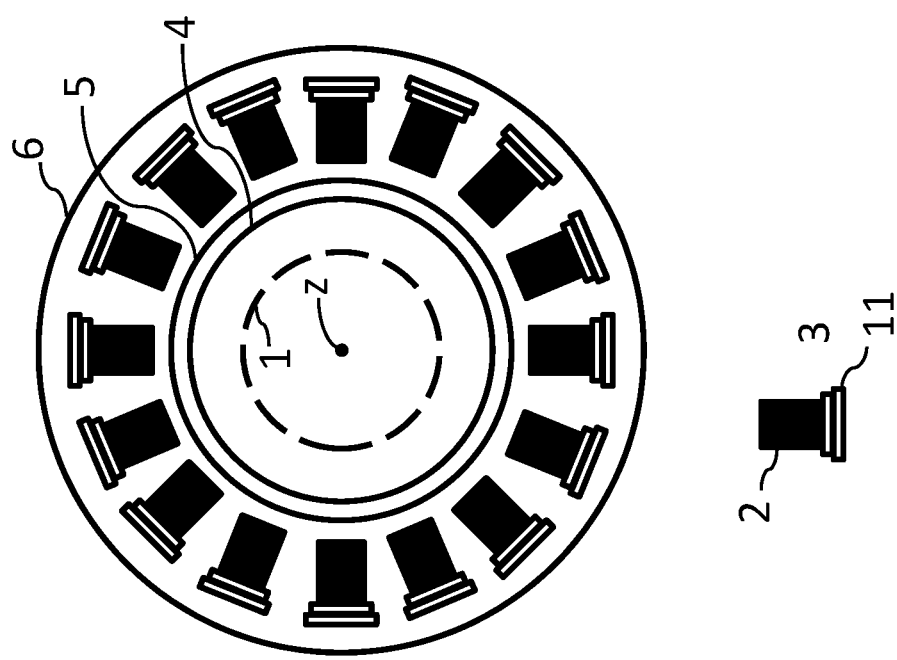
FIG. 1 shows a cross section of the components of an MR/PET hybrid imaging apparatus, arranged radially inside the gradient coil system, having separate internal shielding devices for the PET electronics and the RF resonator structure according to the prior art.

FIG. 1 shows a conventional construction of a hybrid imaging apparatus (here: MR/PET scanner). An RF resonator structure 1 is located at the center of the apparatus here. A PET arrangement having scintillator crystals 2 and a photosensor 3 (having a plurality of sensor elements) for detecting photons produced in the scintillator crystals 2 and having a readout circuit board 11 having PET electronics is arranged radially outside the RF resonator structure 1. An RF coil shield 4 preventing the RF resonator structure 1 from interacting with the environment in the near-field range and thus from being detuned is arranged radially between the RF resonator structure 1 and the PET arrangement. Moreover, the PET arrangement is protected from electromagnetic interacting in the MHz up to the GHz range by an internal PET shielding system 5 and an external PET shielding 6.

Figure 2:
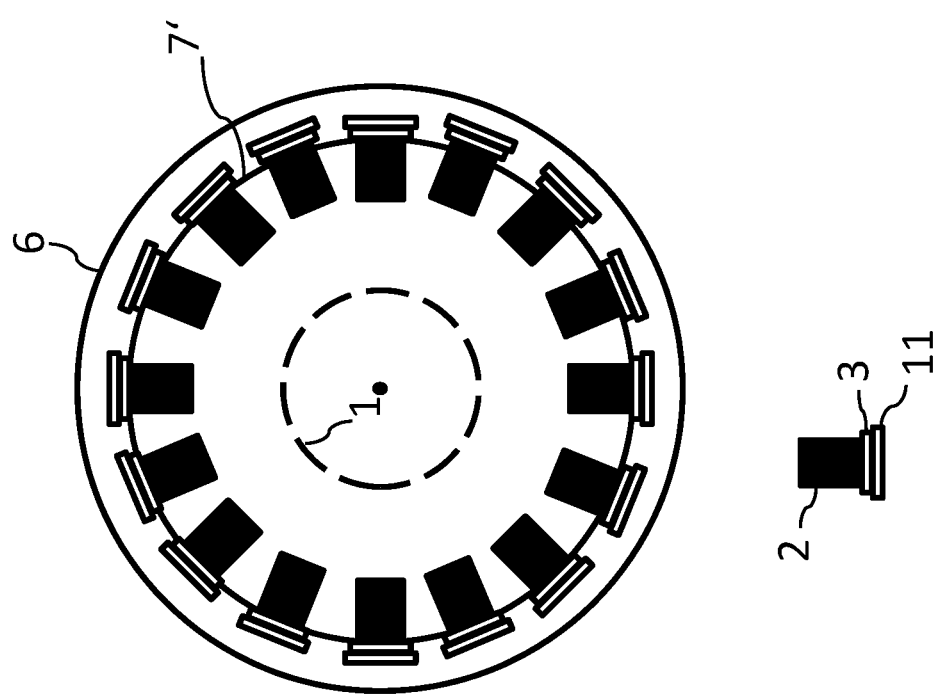
FIG. 2 shows a cross section of the components of an MR/PET hybrid imaging apparatus, arranged radially inside the gradient coil system, having an integrated RF/PET shielding device between scintillator crystals and photosensors according to the prior art.

FIG. 2 shows an MR/PET scanner known from the prior art having an integrated internal shielding device 7', which assumes the functions of the internal PET shielding system 5 and of the RF coil shield 4 from the apparatus shown in FIG. 1. The integrated internal shielding device 7' is located within the PET arrangement between the scintillator crystals 2 and photosensor 3, such that, together with the external PET shielding system 6, it protects the photosensors 3 and the PET electronics against RF radiation of the RF resonator structure 1 and the RF resonator structure 1 is shielded by the integrated internal shielding device 7' against disturbing influences of the PET electronics of the PET arrangement.

Figure 3:
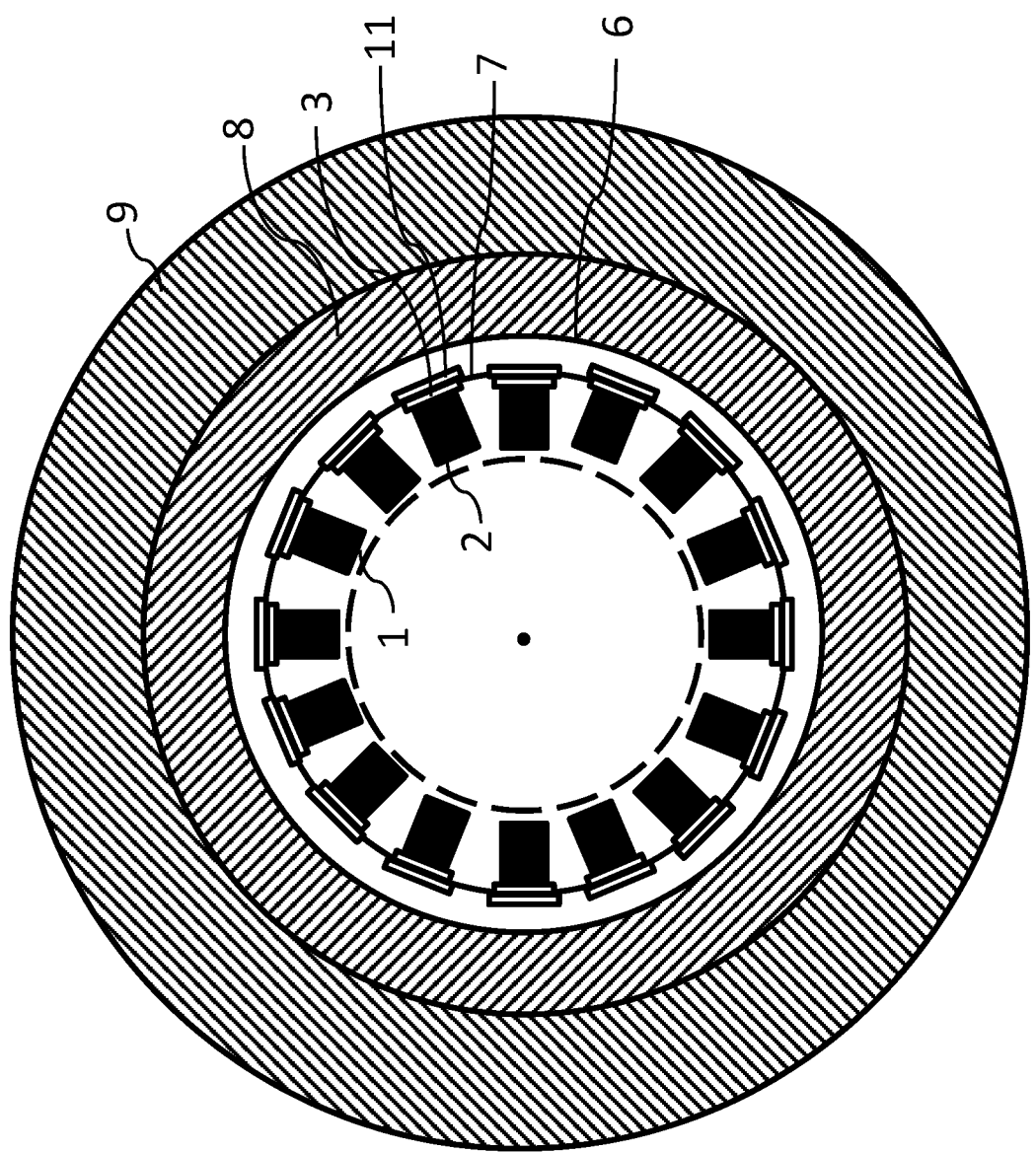
FIG. 3 shows a cross section of an MR/PET hybrid imaging apparatus according to the invention.

FIG. 3 shows a hybrid imaging apparatus according to the present invention having an MR arrangement and a PET arrangement. The MR arrangement comprises, in addition to the RF resonator structure 1, a gradient coil system 8 having a longitudinal axis z and a magnetic coil arrangement 9 for producing a static magnetic field. The PET arrangement with the scintillator crystals 2, photosensor 3 and readout circuit board 11 is arranged radially between the gradient coil system 8 and the RF resonator structure 1. The sensor elements of the photosensor 3 are arranged coaxially (with the longitudinal axis z of the gradient coil system 8 as a common axis), in particular concentrically, with respect to the gradient coil system. In the present example, the photosensor 3 in cross section overall has a circular arrangement of the sensor elements. However, other geometries are also possible, for example an arrangement of the sensor elements along a square cross section or an arrangement, linear in cross section, of the sensor elements on two mutually opposite sections.

Here, too, an external shielding device 6 and an integrated internal shielding device 7 (that is to say a combined PET/RF shielding device) are provided. According to the invention, said internal shielding device 7 is arranged radially outside the photosensor 3 and/or integrated in the photosensor 3. The scintillator crystals 2 can thus occupy the distance between the RF resonator structure 1 and integrated shielding 7 and therefore be arranged close to the RF resonator structure 1, as is shown in FIG. 3. Due to the arrangement according to the invention of the internal shielding device 7 in or radially outside the photosensor 3, the optical photons produced in the scintillator crystals 2 can pass to the photosensor 3 without being obstructed, as a result of which the performance of the hybrid imaging apparatus is improved with respect to the apparatus shown in FIG. 2.

Figure 4:
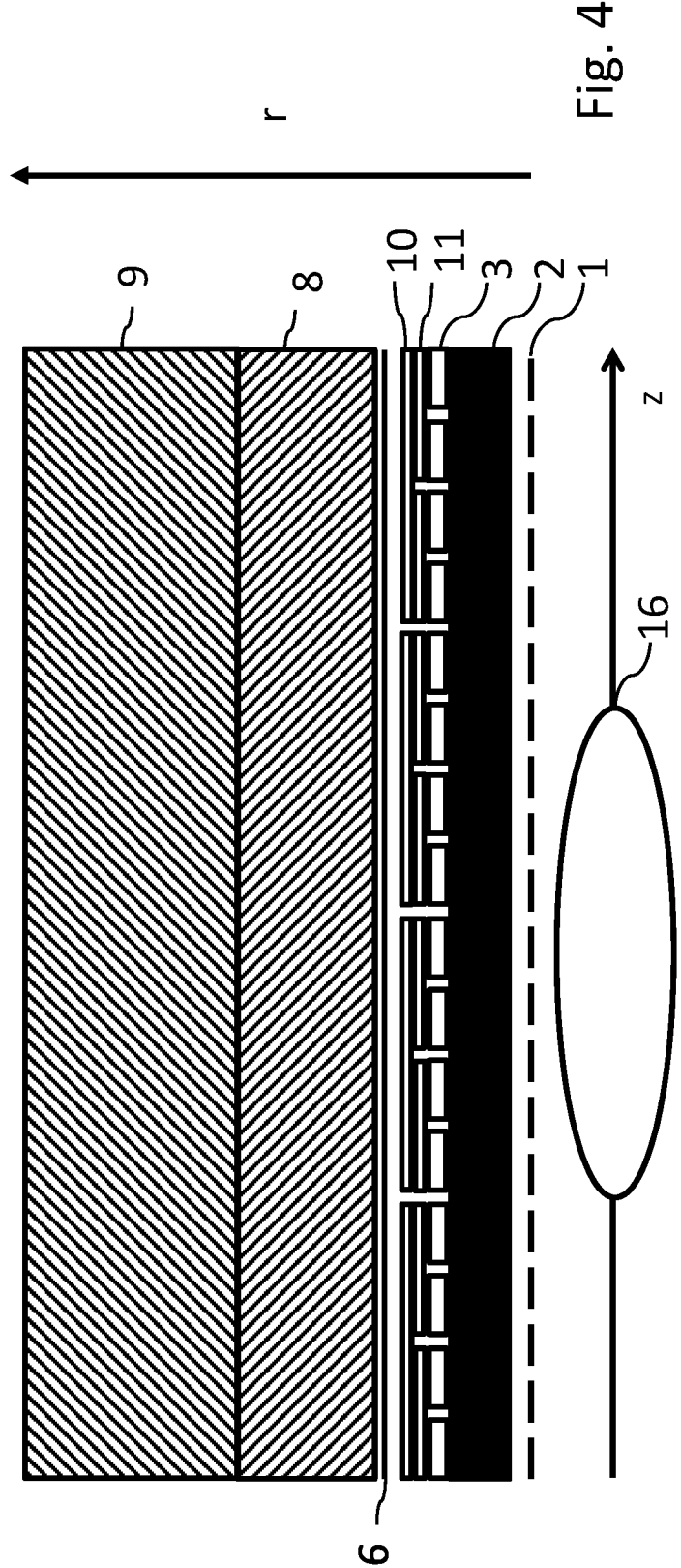
FIG. 4 shows the construction of half of an MR/PET hybrid imaging apparatus (longitudinal section).

FIG. 4 shows the detailed construction of an MR/PET hybrid imaging apparatus (integrated internal shielding device is not illustrated), wherein the radial direction r is plotted toward the top and the axial direction of the longitudinal axis z is plotted toward the right. The photosensor 3 is arranged radially outside, adjoining the scintillator crystals 2, followed by circuit boards (sensor circuit boards 10 and readout circuit boards 11 with PET electronics). The high-energy photons (gamma radiation) coming from an examination object 16 arranged at the center of the apparatus within the RF resonator structure 1 pass into the scintillator crystals 2, where optical photons (that is to say photons in the UV or visible wavelength range) are produced that are detected by the photosensor 3 that is in turn arranged radially further outside. The outermost shielding device 6 is arranged radially between the circuit boards 10, 11 and the gradient coil system 8.

Figure 5:
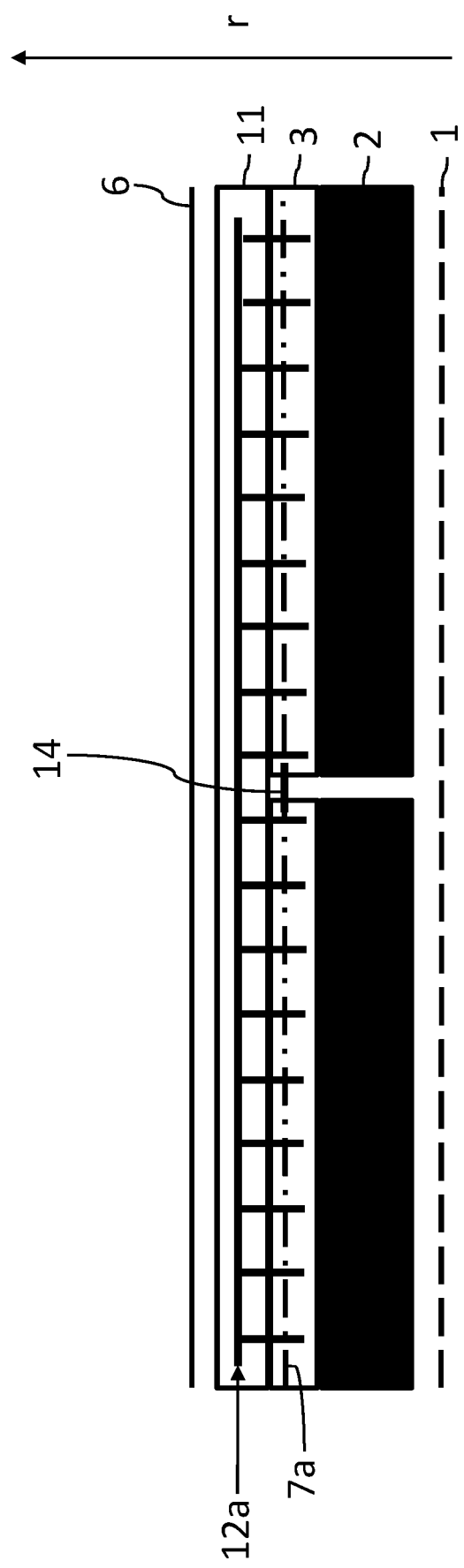
FIG. 5 shows a detail of a first embodiment of the shielding concept according to the invention having an internal shielding device in the photosensor (longitudinal section).

FIG. 5 shows the arrangement of an integrated internal shielding device 7a (shown in dashed-dotted lines) for a first variant of the hybrid imaging apparatus according to the invention. The internal shielding device 7a is integrated in the photosensor 3 here. To ensure transmission without obstruction of the photoelectrons generated in the photosensor 3 through the internal shielding device 7a into the circuit boards that are arranged thereabove (here: readout circuit boards 11), vias 12a are provided in the photosensor 3.

Figure 8:
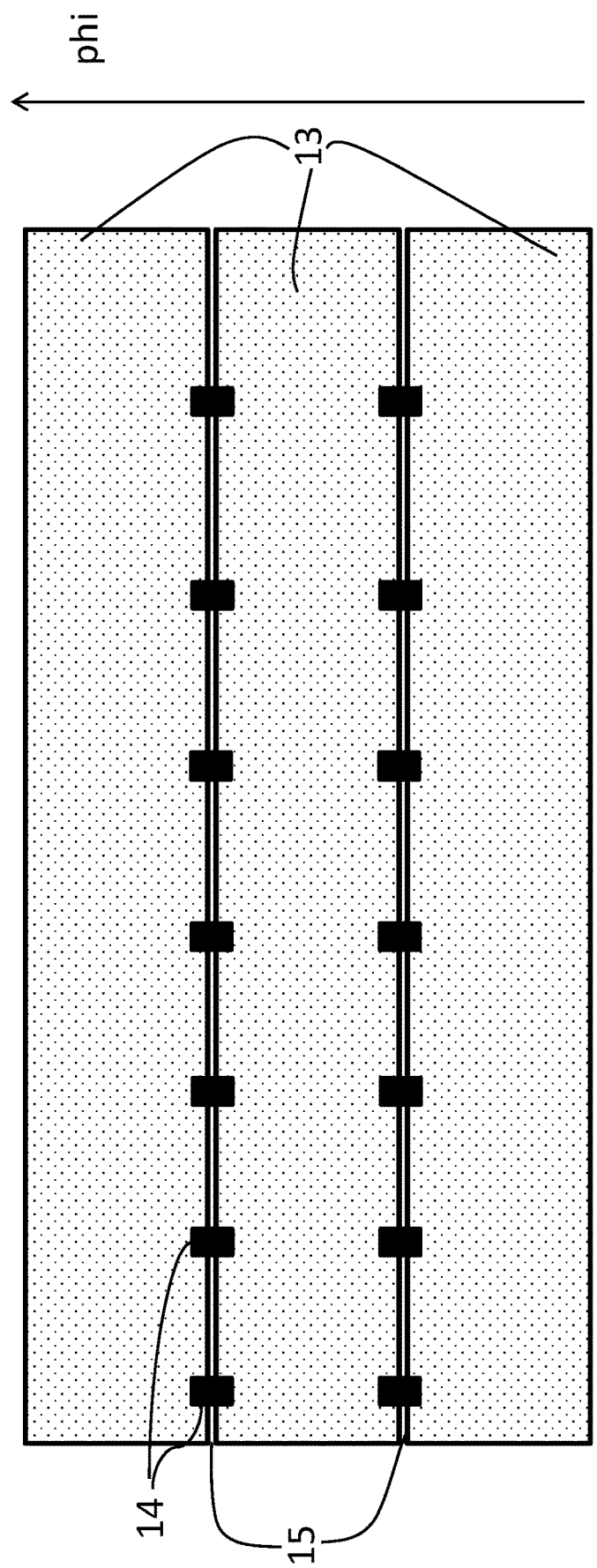
FIG. 8 shows a plan view of a detail of an internal shielding device having a plurality of shielding faces that are capacitively coupled with capacitors (developed view).

The internal shielding device 7a is distributed over a plurality of sensor elements of the photosensor 3 and comprises a plurality of shielding faces 13 that are interconnected through shielding connections 14 (see also FIG. 8).

Figure 6:
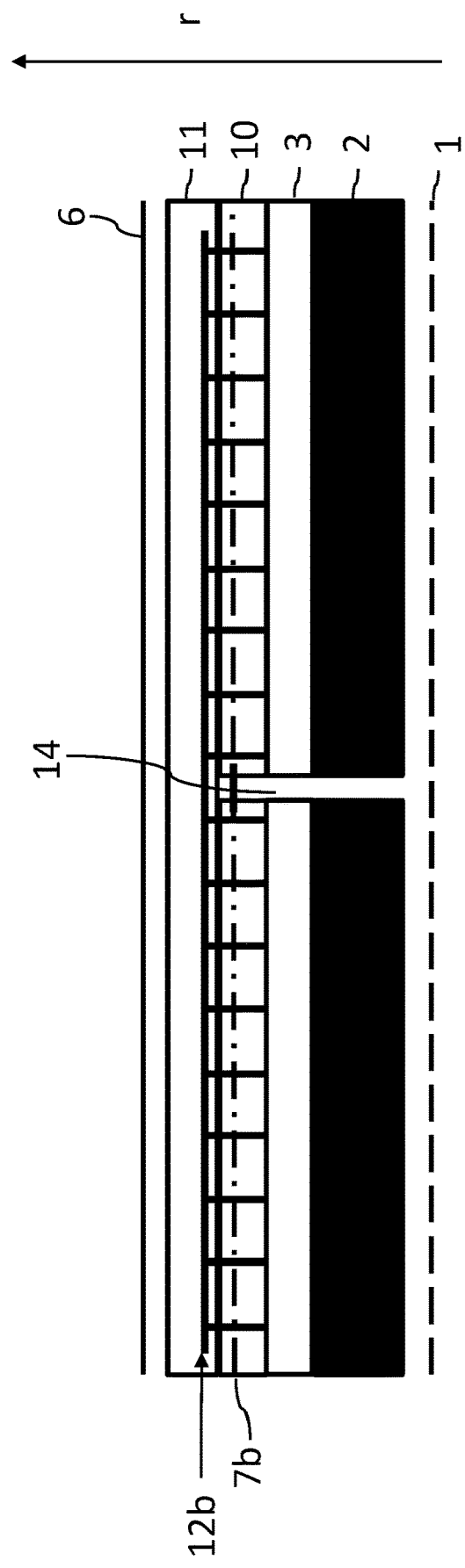
FIG. 6 shows a detail of a second embodiment of the shielding concept according to the invention having an internal shielding device in the sensor circuit board (longitudinal section).

In a second variant, shown in FIG. 6, an integrated internal shielding device 7b (illustrated in dashed-dotted lines) is integrated in the sensor circuit boards 10, wherein electrically conducting circuit board layers of the sensor circuit boards 10 form the internal shielding device 7b or are part of the internal shielding device 7b. The photosensor 3 is connected to the readout circuit boards 11 that are arranged radially outside the internal shielding device 7b over vias 12b in the sensor circuit boards 10.

Figure 7:
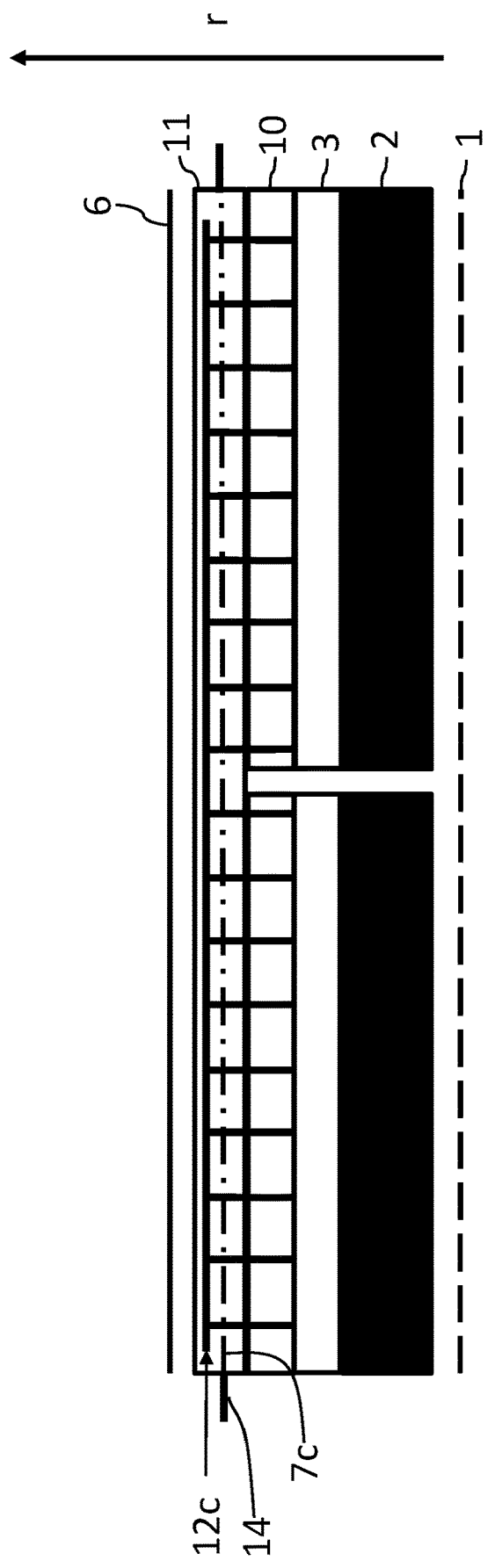
FIG. 7 shows a detail of a third embodiment of the shielding concept according to the invention having an internal shielding device in the readout circuit board (longitudinal section).

In a third variant, shown in FIG. 7, an integrated internal shielding device 7c (illustrated in dashed-dotted lines) is integrated in the readout circuit boards 11, wherein electrically conducting circuit board layers of the readout circuit boards 11 form the internal shielding device 7c or are part of the internal shielding device 7c. The photosensor 3 is connected to the components of the readout circuit boards 11 that are arranged radially outside the internal shielding device 7b over vias 12c in the sensor circuit boards 10 and the readout circuit boards 11.

The internal shielding device 7, 7a, 7b, 7c according to the invention comprises a plurality of shielding faces 13 that are capacitively coupled to one another. This can be effected for example with capacitors 14, as is illustrated in FIG. 8 in a developed view. The shielding faces 13 are arranged here adjacently in the circumferential direction phi and are separated from one another by slits 15 that are bridged by the capacitors 14.

FIG. 9 shows another option of capacitive coupling of shielding faces 13a, 13b in a sectional illustration perpendicular to the axial direction z of the apparatus. In the embodiment shown in FIG. 9, the shielding faces 13a, 13b are arranged in two layers that are located at a radial distance from one another, wherein the shielding faces 13a, 13b overlap in the circumferential direction u, as a result of which the desired capacitive coupling is attained.

A closed RF shield face is produced by way of the capacitive couplings of the shielding faces shown in FIG. 8 and FIG. 9. Said RF shield face can form, together with the external shielding device, a closed shielding system for the ET electronics by virtue of connecting the integrated internal shielding device to the external shielding device by way of further RF shield faces (not shown).

According to the invention, an integrated EP/RF shielding device is positioned behind the (radially outside) or in the photosensor to ensure that a large number of the photons produced in the scintillator crystals is detected. In this way, a compact hybrid imaging apparatus having optimized performance is realized more cost-effectively.

LIST OF REFERENCE SIGNS

1 RF resonator structure
2 Scintillator crystals
3 Photosensors
4 RF coil shield
5 Internal PET shielding system
6 External PET shielding system
7 Integrated internal shielding device
7a Integrated internal shielding device
7b Integrated internal shielding device
7c Integrated internal shielding device
7' Integrated internal shielding device according to the prior art
8 Gradient coil system
9 Magnetic coil arrangement for static magnetic field
10 Sensor circuit board
11 Readout circuit board
12a Vias in the photosensor
12b Vias in the sensor circuit board
12a Vias in the readout circuit board
13 Shielding faces
13a Radially outwardly located shielding faces
13b Radially inwardly located shielding faces
14 Shielding connections, in particular capacitors
15 Slits
16 Examination object
phi Circumferential direction
r Radial direction in relation to the longitudinal axis of the MRI arrangement
z Longitudinal axis of the gradient coil system

LIST OF LITERATURE

[1] Berneking, Arne, et al. "Design and Characterization of a Gradient-Transparent RF Copper Shield for PET Detector Modules in Hybrid MR-PET Imaging." IEEE Transactions on Nuclear Science 64.5 (2017): 1118-1127.

[2] Berneking, Arne, et al. "RF Coil Performances in Compact Hybrid MR/PET Scanner Design Using an Integrated Shielding", ISMRM 2017
[3] C Parl, A Kolb, A M Schmid, H F Wehrl, J A Disselhorst, P D Soubiran, D StrickerShaver and B J Pichler "A novel optically transparent RF shielding for fully integrated PET/MRI systems." Phys. Med. Biol. 62 (2017) 7357-7378
[4] U.S. Pat. No. 9,072,451 B2
[5] Truhn, Daniel, F. Kiessling, and V. Schulz. "Optimized RF shielding techniques for simultaneous PET/MR." Medical physics 38.7 (2011): 3995-4000.
[6] Salomon, André, et al. "Sparse crystal setting and large axial FOV for integrated wholebody PET/MR." Nuclear Science Symposium and Medical Imaging Conference (NSS/MIC), 2011 IEEE. IEEE, 2011.
[7] US 20060293580 A1
[8] L. Yin, N. Groß-Weege, D. Schug, and V. Schulz "Evaluation of materials for sharedvolume PET/MRI inserts," NSS/MIC Conference 2017, Abstract #2531
[9] US20130211233 A
[10] US2014264041A
[11] U.S. Pat. No. 7,667,457 B2
[12] J. Jin, Elektromagnetic Analysis and Design, Design of RF Shield, CRC Press, 1999

What is claimed is:

1. A hybrid imaging apparatus comprising
a magnetic resonance imaging (MRI) arrangement having a radio frequency (RF) resonator structure and a gradient coil system with a longitudinal axis,
an emission tomography (ET) arrangement having a detector device comprising a photosensor and a circuit board arrangement with at least one readout circuit board on which an ET electronics is arranged,
an internal shielding device configured to mutually shield the ET electronics of the ET arrangement and the RF resonator structure of the MRI arrangement,
wherein the photosensor is arranged, in relation to the longitudinal axis, radially inside the circuit board arrangement and radially outside the RF resonator structure, and
wherein the internal shielding device is arranged, in relation to the longitudinal axis, radially outside the photosensor and/or integrated into the photosensor.

2. The hybrid imaging apparatus as claimed in claim 1, wherein the emission tomography arrangement is a positron emission tomography (PET) arrangement, wherein the photosensor comprises a plurality of circularly arranged sensor elements.

3. The hybrid imaging apparatus as claimed in claim 1, wherein the internal shielding device comprises a plurality of shielding faces made from an electrically conductive material.

4. The hybrid imaging apparatus as claimed in claim 3, wherein the plurality of shielding faces are overlapping shielding faces.

5. The hybrid imaging apparatus as claimed in claim 3, wherein the shielding faces are integrated into at least one circuit board of the circuit board arrangement or are arranged on at least one circuit board of the circuit board arrangement, and wherein the at least one circuit board is a readout circuit board and/or a sensor circuit board of the ET arrangement.

6. The hybrid imaging apparatus as claimed in claim 5, wherein the circuit board arrangement is multilayered and comprises at least partially a plurality of shielding faces, wherein the plurality of shielding faces are distributed within the circuit board arrangement over a plurality of layers of the circuit board arrangement.

7. The hybrid imaging apparatus as claimed in claim 5, wherein the shielding faces within the circuit board arrangement are capacitively connected to one another.

8. The hybrid imaging apparatus as claimed in claim 7, wherein the capacitive connection of the shielding faces within the circuit board arrangement is configured through an overlay of the shielding faces within the circuit board arrangement.

9. The hybrid imaging apparatus as claimed in claim 1, wherein the internal shielding device forms a closed RF shield face.

10. The hybrid imaging apparatus as claimed in claim 1, further comprising an external shielding device that is arranged radially outside the detector device and the circuit board arrangement.

11. The hybrid imaging apparatus as claimed in claim 10, wherein the external shielding device is electrically connected or electromagnetically coupled to the internal shielding device.

12. The hybrid imaging apparatus as claimed in claim 10, wherein components of the ET electronics are arranged between the internal shielding device and the external shielding device.

13. The hybrid imaging apparatus as claimed in claim 10, further comprising signal and supply lines of the ET electronics arranged between the internal shielding device and the external shielding device.

14. The hybrid imaging apparatus as claimed in claim 1,
wherein the internal shielding device is integrated into at least one sensor circuit board of the circuit board arrangement and the at least one sensor circuit board comprises vias configured to receive signal and supply lines or
wherein the internal shielding device is integrated into the photosensor and the photosensor comprises vias through the internal shielding device that is integrated into the photosensor.

15. The hybrid imaging apparatus as claimed in claim 1, wherein the detector device is a silicon photomultiplier (SiPM).

* * * * *